(12) United States Patent
Politis

(10) Patent No.: US 11,684,727 B2
(45) Date of Patent: Jun. 27, 2023

(54) PEN NEEDLE APPARATUS

(71) Applicant: Embecta Corp., Andover, MA (US)

(72) Inventor: Victor Politis, Norwood, MA (US)

(73) Assignee: Embecta Corp., Andover, MA (US)

( * ) Notice: Subject to any disclaimer, the term of this patent is extended or adjusted under 35 U.S.C. 154(b) by 361 days.

(21) Appl. No.: 16/967,872

(22) PCT Filed: Feb. 7, 2019

(86) PCT No.: PCT/US2019/017044
§ 371 (c)(1),
(2) Date: Aug. 6, 2020

(87) PCT Pub. No.: WO2019/157176
PCT Pub. Date: Aug. 15, 2019

(65) Prior Publication Data
US 2021/0046254 A1 Feb. 18, 2021

Related U.S. Application Data

(60) Provisional application No. 62/629,564, filed on Feb. 12, 2018.

(51) Int. Cl.
*A61M 5/34* (2006.01)
*A61M 5/32* (2006.01)

(52) U.S. Cl.
CPC .......... *A61M 5/347* (2013.01); *A61M 5/3293* (2013.01)

(58) Field of Classification Search
CPC .............. A61M 5/3286; A61M 5/3293; A61M 5/3291; A61M 5/347; A61M 5/344;
(Continued)

(56) References Cited

U.S. PATENT DOCUMENTS

2006/0229562 A1 10/2006 Marsh et al.
2007/0149924 A1 6/2007 Marsh
(Continued)

FOREIGN PATENT DOCUMENTS

CN 103007395 A 4/2013
CN 205885909 U 1/2017
(Continued)

OTHER PUBLICATIONS

International Search Report dated May 7, 2019, which issued in counterpart PCT Patent Application No. PCT/US19/017044.

*Primary Examiner* — Theodore J Stigell
*Assistant Examiner* — Rachel T. Smith
(74) *Attorney, Agent, or Firm* — Greenberg Traurig, LLP; Roman Fayerberg; David J. Dykeman

(57) ABSTRACT

A pen needle (30, 110) is disclosed for coupling to a delivery device (10) and piercing a septum on the delivery device. The pen needle includes a collar (32, 112) having a side wall (36, 116), an open proximal end (38), and a distal end (40, 118) having a coupling member (50). The pen needle also includes a needle hub (34, 114) having a proximal end (50, 124) and a distal end (58, 126), where the proximal end of the needle hub has a coupling member coupled to the distal end of the collar. The needle hub rotates independently of the collar. A needle (52) extends from the distal end of the needle hub, and a projection (76, 126) extends from the proximal end of the needle hub for piercing a septum (106) of a delivery device. The collar (32, 112) rotates independently from the needle hub (34, 114) so that the collar screws onto the threaded end of the delivery device while the needle hub does not rotate and the projection advances to pierce the septum (106) without rotating.

24 Claims, 11 Drawing Sheets

(58) Field of Classification Search
CPC .......... A61M 5/34; A61M 5/345; A61M 5/32; A61M 2005/3228
See application file for complete search history.

(56) References Cited

U.S. PATENT DOCUMENTS

| | | |
|---|---|---|
| 2010/0292656 A1 | 11/2010 | Groskopf et al. |
| 2011/0257603 A1 | 10/2011 | Ruan et al. |
| 2012/0150125 A1 | 6/2012 | Karlsson et al. |
| 2012/0150128 A1 | 6/2012 | Zhao |
| 2012/0277685 A1* | 11/2012 | Limaye ............... A61M 5/3202 604/192 |
| 2015/0328412 A1 | 11/2015 | Bates et al. |
| 2018/0169350 A1* | 6/2018 | Knapp .................. A61M 5/347 |

FOREIGN PATENT DOCUMENTS

| | | |
|---|---|---|
| CN | 107405456 A | 11/2017 |
| CN | 209695987 U | 11/2019 |
| JP | 2007111156 A | 5/2007 |
| JP | 2012232136 A | 11/2012 |
| JP | 2013500745 A | 1/2013 |
| JP | 2015526221 A | 9/2015 |
| WO | 2016196518 A1 | 12/2016 |

\* cited by examiner

PEN NEEDLE APPARATUS

This application claims priority to U.S. Provisional Patent Application No. 62/629,564, filed on Feb. 12, 2018, which is hereby incorporated by reference in its entirety.

FIELD OF THE INVENTION

The present invention relates generally to a pen needle for coupling to a delivery device, such as a pen needle delivery device. The pen needle includes a cannula or needle for delivering the substance to a patient and a projection for piercing a septum of the delivery device. The pen needle is configured for coupling to the delivery device without rotating the projection relative to the septum when the projection pierces the septum of the delivery device.

BACKGROUND OF THE INVENTION

Insulin and other injectable medications are commonly delivered with drug delivery pens, where a disposable pen needle hub is attached to the pen to facilitate access to the drug container and allow fluid egress from the container through the needle into the patient.

Various pen needle delivery devices are known in the art for dispensing the substance to the patient. The delivery devices often use a disposable needle hub having a cannula or needle extending from a patient end of the hub for inserting into the patient. A non-patient end of the hub is coupled to the pen delivery device for delivering the substance to the patient.

The needle hub assembly is often packaged in a container containing several loose needle hubs. A needle hub is selected from the package and attached to the pen needle delivery device for injecting the patient and then removed to be discarded. The needle hub package includes an outer cover that encloses the needle hub and a removable seal that is peeled from the outer cover to open the cavity so that the needle hub can be removed. The needle hub can have threaded non-patient end that is threaded onto the delivery device. The delivery device with the attached needle hub is then removed from the outer cover. An inner needle shield is attached to the needle hub to cover the cannula until the device is ready for use. The shield is removed to expose the cannula for use to deliver the substance to the patient. After use, the needle hub can be inserted back into the outer cover to enclose the exposed cannula. The pen delivery device is separated from the needle hub leaving the needle hub within the outer cover.

The pen needles often include a needle that extends from the proximal, non-patient end of the needle hub. The needle is positioned to pierce the septum of the delivery pen to access the drug or other medication. The pen needle is threaded onto the end of the delivery pen so that the needle pierces the septum as the needle hub advances onto the delivery pen. The needle typically has a thin diameter which can bend during the insertion into and though the septum, which interferes with the delivery of the drug to the patient.

Existing pen needle assemblies are disclosed in U.S. Patent Application Publication Nos. 2006/0229562 to Marsh et al. and 2007/0149924 to R. Marsh, the entire contents of both of which are hereby incorporated by reference.

Although the prior devices have been suitable for the intended use, there is a continuing need in the industry for improved pen needle devices and methods of connecting the pen needle to the delivery device.

SUMMARY OF THE INVENTION

The present invention relates generally to a pen needle for coupling to a delivery device such as a pen needle delivery device used for insulin delivery injections. The pen needle includes a needle or cannula for delivering the substance to a patient. The pen needle includes a threaded hub that is configured for connecting to the delivery device.

The pen needle in one embodiment includes a projection extending from a non-patient proximal end for piercing a septum of the delivery device to access the drug or other substance to be delivered to the patient. The pen needle includes a needle or cannula extending from the distal end for piercing the skin of the patient and delivering the substance. The pen needle is configured for coupling to the delivery device without rotating the projection with respect to the delivery device when the projection pierces the septum of the delivery device.

In one embodiment, the pen needle has a threaded collar and a needle hub where the collar can rotate relative to the needle hub. The collar is threaded onto a threaded end of the delivery device while the needle hub and projection remain rotationally fixed. The needle hub moves axially by the rotation of the threaded collar whereby the projection moves axially to pierce the septum without the projection rotating relative to the septum and the collar.

The needle hub is coupled to the collar where the collar can rotate independently of the needle hub. The needle hub includes a coupling mechanism to enable the needle hub and collar to rotate relative to the other.

In one embodiment, the coupling between the collar and the needle hub is a flange on one of the needle hub or collar that mate with a recess on the other of the needle hub or collar. The collar can have an open end defined by an inwardly extending flange that is received in an annular recess in the needle hub.

In another embodiment, the coupling can be two spaced apart flanges extending outwardly from the needle hub to define an annular recess. The top distal end of the collar is received in the annular recess of the needle hub to allow rotation of the collar relative to the needle hub.

In a further embodiment, the coupling is a flange on the needle hub and at least one tab projecting outwardly from the needle hub and spaced from the flange. The space between the flange and the tab captures the top end of the collar so that the collar can rotate relative to the needle hub.

The features of the pen needle are basically obtained by providing the pen needle with a collar having a side wall, an open proximal end, and a distal end; and a needle hub. The needle hub is rotatably coupled to the distal end of the collar. The needle hub has a proximal end and a distal end. A needle extends from the distal end, and a projection extends from the proximal end of the needle hub. The projection is configured for piercing a septum of a delivery device when the pen needle is connected to the delivery device. The collar is rotatable independently of the needle hub and the projection so that the needle hub can remain rotationally fixed when the collar is rotated and attached to the delivery device. The needle hub is able to move axially with the axial movement of the collar.

The features are further obtained by providing a pen needle with a collar and a needle hub. The collar has a side wall, an open proximal end having a coupling member, and a distal end. The needle hub has a proximal end and a distal end. The proximal end of the needle hub has a coupling member coupled to the distal end of the collar where the collar is rotatable independently of the needle hub. A needle extends from the distal end of the needle hub, and a projection extends from the proximal end of the needle hub. The projection is configured for piercing a septum of a delivery device when the pen needle is attached to the delivery device.

The features of the invention are also obtained by providing a method of assembling a pen needle to a pen needle delivery device. The method comprises inserting the pen needle delivery device into a pen needle, where the pen needle includes a threaded collar having a proximal end and distal end, and a needle hub having a proximal end rotatably coupled to the distal end of the collar and a distal end with a needle extending from the distal end. The needle hub has a projection extending toward the proximal end of the needle hub. The collar rotates relative to the pen needle delivery device without rotating the needle hub to pierce a septum on the pen needle delivery device The objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which.

Throughout the drawings, like reference numbers will be understood to refer to like parts, components, and structures.

DETAILED DESCRIPTION OF THE EXEMPLARY EMBODIMENTS

Figure 1:
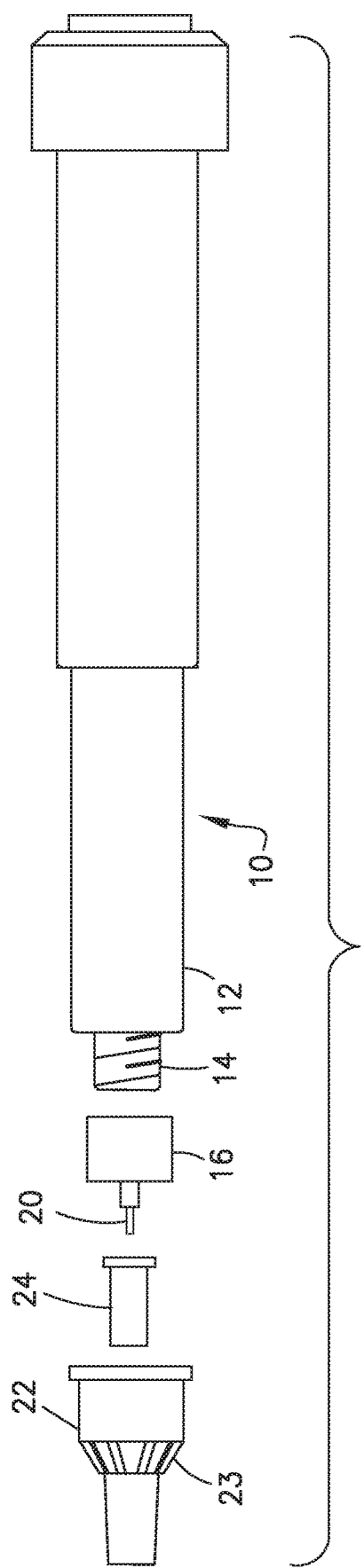
FIG. 1 is an exploded perspective view of a pen needle delivery device showing a pen needle assembly that includes a needle hub supporting a cannula, inner shield, and outer cover.

The present invention is directed to a pen needle for connecting to a delivery device such as a pen needle delivery device. The pen needle supports a needle or cannula for delivering the substance to the patient and includes a projection for piercing a septum on the delivery device when the pen needle is attached to the delivery device. Pen needle is configured so that the projection moves in a linear direction substantially without rotation relative to the delivery device for piercing the septum on the delivery device when the pen needle is attached to the delivery device.

Reference to embodiments of the present invention are illustrated in the accompanying drawings, wherein like reference numerals refer to like elements throughout. The embodiments described herein exemplify, but do not limit, the present invention by referring to the drawings. The exemplary embodiments are presented in separate descriptions, although the individual features and construction of these embodiments can be combined in any number of ways to meet the therapeutic needs of the user.

It will be understood by one skilled in the art that this disclosure is not limited in its application to the details of construction and the arrangement of components set forth in the following description or illustrated in the drawings. The embodiments herein are capable of being modified, practiced or carried out in various ways. It will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not limited to physical or mechanical connections or couplings. Further, terms such as up, down, bottom, and top are relative, and are employed to aid illustration, but are not limiting. Features of the different embodiments can be combined with features of other embodiments so long as they are not inconsistent with each other.

Pen needle delivery device 10, as shown in FIG. 1 typically comprises a dose knob/button, an outer sleeve 12, and a cap. A dose knob/button allows a user to set the dosage of medication to be injected. The outer sleeve 12 is gripped by the user when injecting medication. The cap is used by the user to securely hold the pen needle device 10 in a shirt pocket or other suitable location and provide cover/protection from accidental needle injury.

Figure 2:
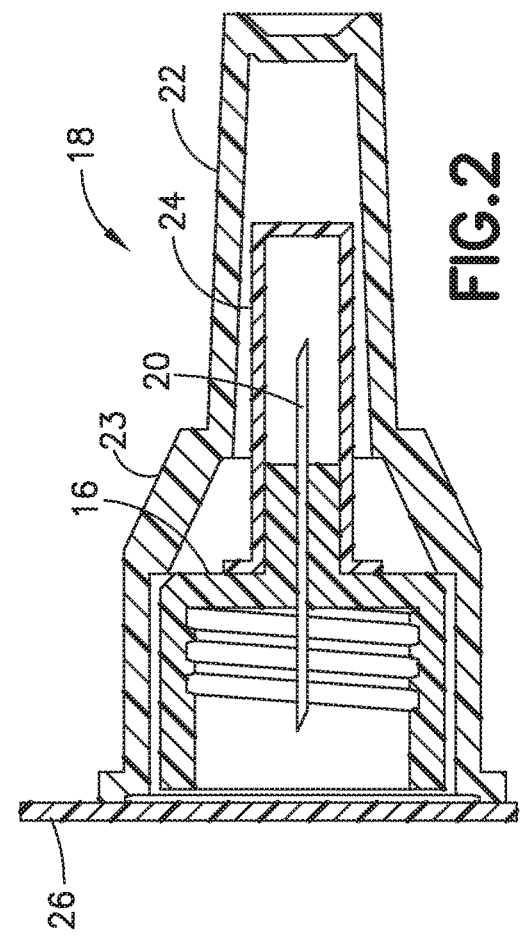
FIG. 2 is a cross-sectional view of the pen needle of FIG. 1.
Figure 3:
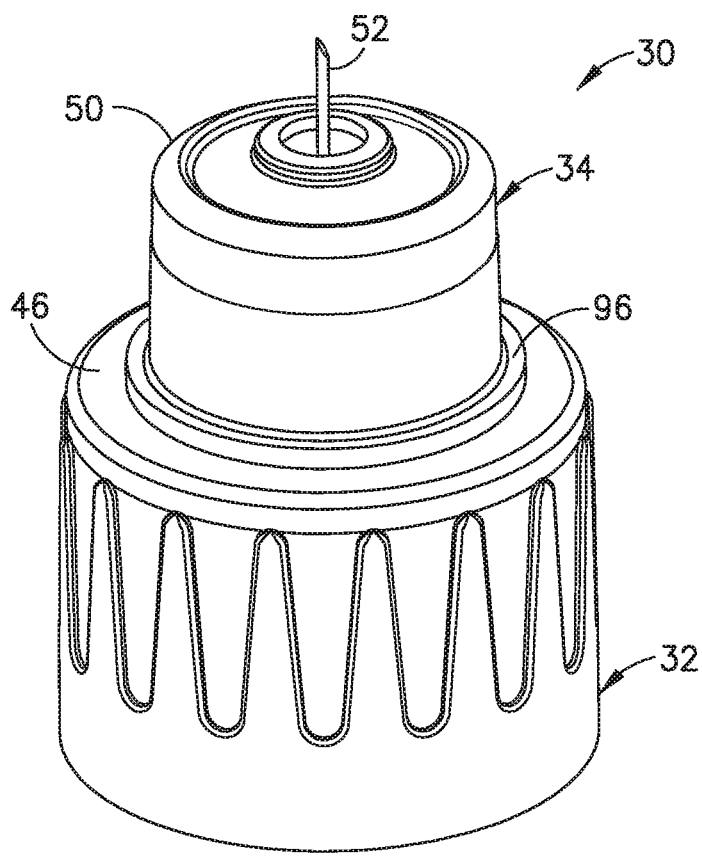
FIG. 3 is a perspective view of the pen needle in one embodiment.

In standard pen needle devices the dosing and delivery mechanisms are all found within the outer sleeve 12 and is not described in greater detail here as they are understood by those knowledgeable of the prior art. A medicament cartridge is typically attached to a standard pen injector housing by known attachment means. The distal movement of a plunger or stopper within the medicament cartridge forces the medication into the reservoir housing. The medicament cartridge is sealed by a septum and punctured by a septum penetrating needle cannula located within a reservoir or housing. Reservoir housing is preferably screwed onto the medicament cartridge although other attachment means can be used. The pen needle delivery device can be a standard pen delivery device known in the industry so that the pen needle delivery device is not shown in detail. The pen needle assembly 10 as shown in FIG. 2 includes a needle hub 16 supporting a cannula 20, an outer cover 22, and an inner shield 24. A protective seal 26 is attached to the open end of the outer cover as shown in FIG. 2 to enclose the needle hub and cannula to maintain a clean and sterile condition. The seal 26 can be a label or other closure member that can be easily peeled from the outer cover to access the needle hub during use.

In standard pen needle devices the dosing and delivery mechanisms are all found within the outer sleeve 12 and is not described in greater detail here as they are understood by those knowledgeable of the prior art. A medicament cartridge is typically attached to a standard pen injector housing by known attachment means. The distal movement of a plunger or stopper within the medicament cartridge forces the medication into the reservoir housing. The medicament cartridge is sealed by a septum and punctured by a septum penetrating needle cannula located within a reservoir or housing. Reservoir housing is preferably screwed onto the medicament cartridge although other attachment means can be used. The pen needle delivery device can be a standard pen delivery device known in the industry so that the pen needle delivery device is not shown in detail. The pen needle assembly 18 as shown in FIG. 2 includes a needle hub 16 supporting a cannula 20, an outer cover 22, and an inner shield 24. A protective seal 26 is attached to the open end of the outer cover as shown in FIG. 2 to enclose the needle hub and cannula to maintain a clean and sterile condition. The seal 26 can be a label or other closure member that can be easily peeled from the outer cover to access the needle hub during use.

Referring to FIGS. 3-13, a first embodiment of the pen needle is shown. The pen needle 30 in the embodiment shown includes a collar 32 and a needle hub 34. The needle hub 34 is coupled to the collar 32 by a suitable coupling mechanism so that the collar 32 can rotate freely about a longitudinal axis relative to the needle hub 34. The needle hub 34 and collar 32 are typically made of a rigid plastic material. In the embodiment shown, the needle hub 34 and collar 32 are made as separate elements that are assembled to form the pen needle 30.

Figure 4:
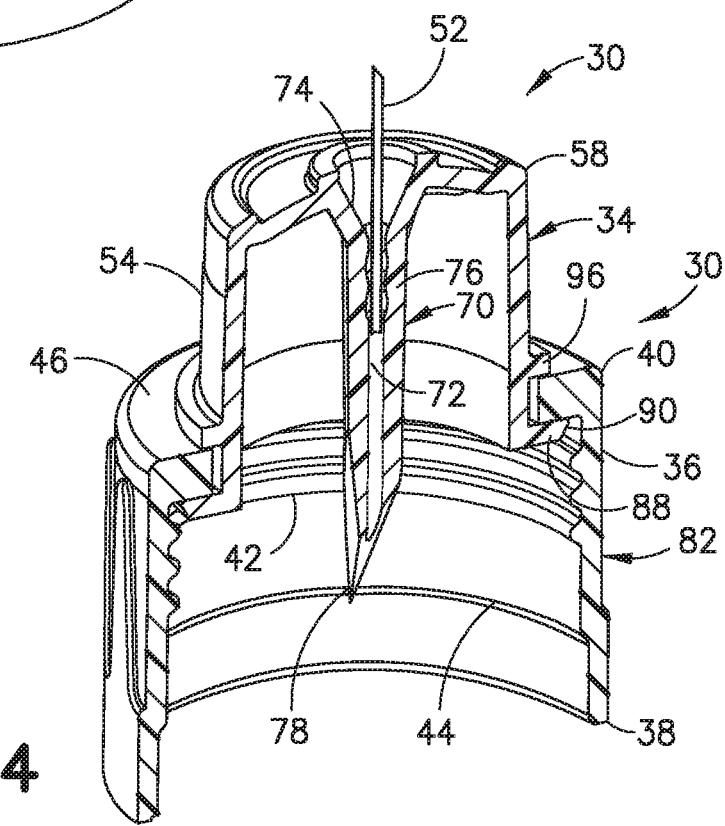
FIG. 4 is a perspective view in cross-section of the pen needle of FIG. 3.
Figure 5:
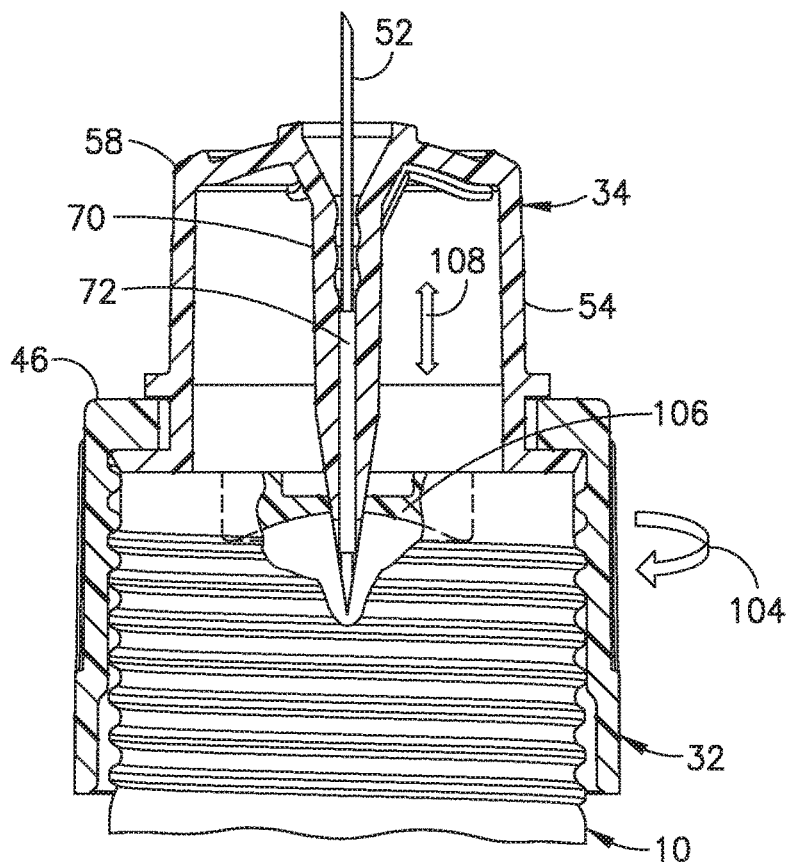
FIG. 5 is a cross-sectional side view of the pen needle showing the collar and needle hub coupled to the delivery device.

As shown in FIG. 4 and FIGS. 6-8, the collar 32 is configured for connecting to the end of the delivery device such as the pen needle delivery device of FIG. 1. In the embodiment shown, the collar 32 has a sidewall 36 forming an open proximal end 38 and a distal end 40. The proximal end is open for coupling with the delivery device as shown in FIG. 5. The sidewall 36 has an inner surface with internal threads 42 for connecting with the delivery device. A chamfered edge 44 as shown in FIG. 4 forms a seal with the delivery device and forms a slightly larger opening for ease of insertion of the delivery device into the open end of the collar 32.

Figure 6:
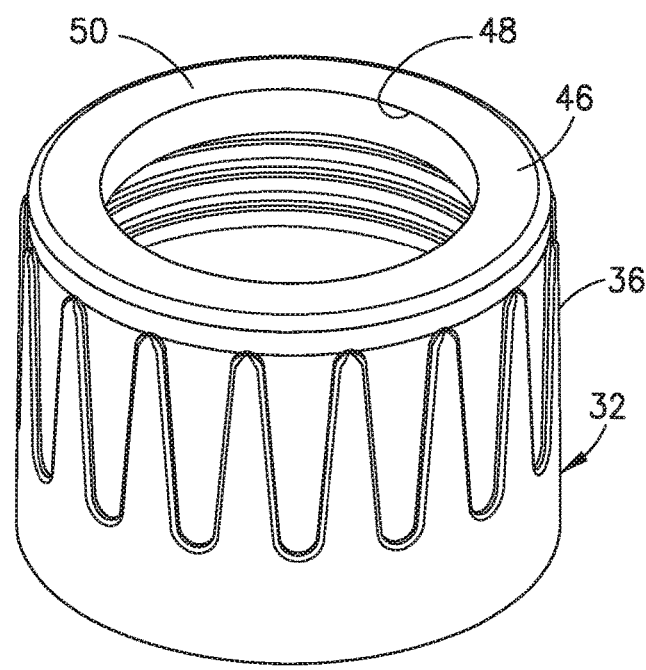
FIG. 6 is a perspective view of the collar of the pen needle of FIG. 3.
Figure 7:
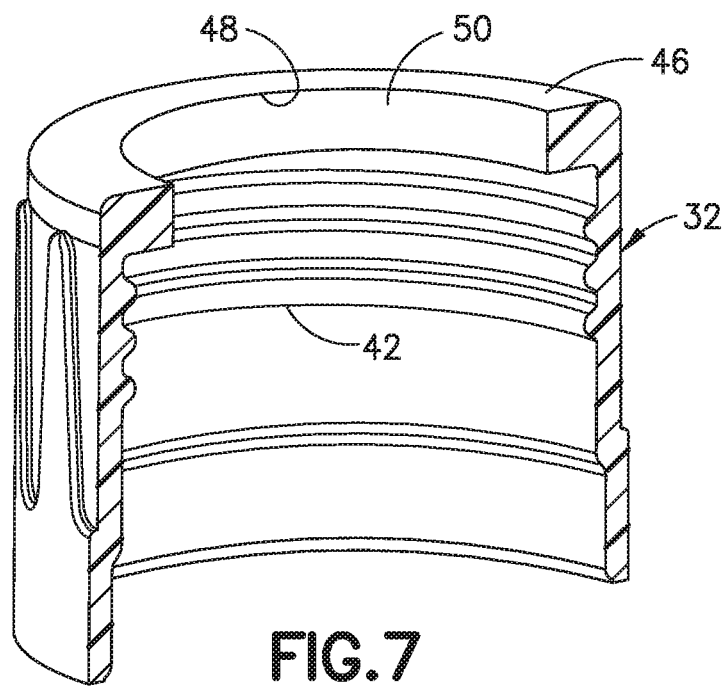
FIG. 7 is a perspective view in cross-section of the collar of FIG. 6.
Figure 8:
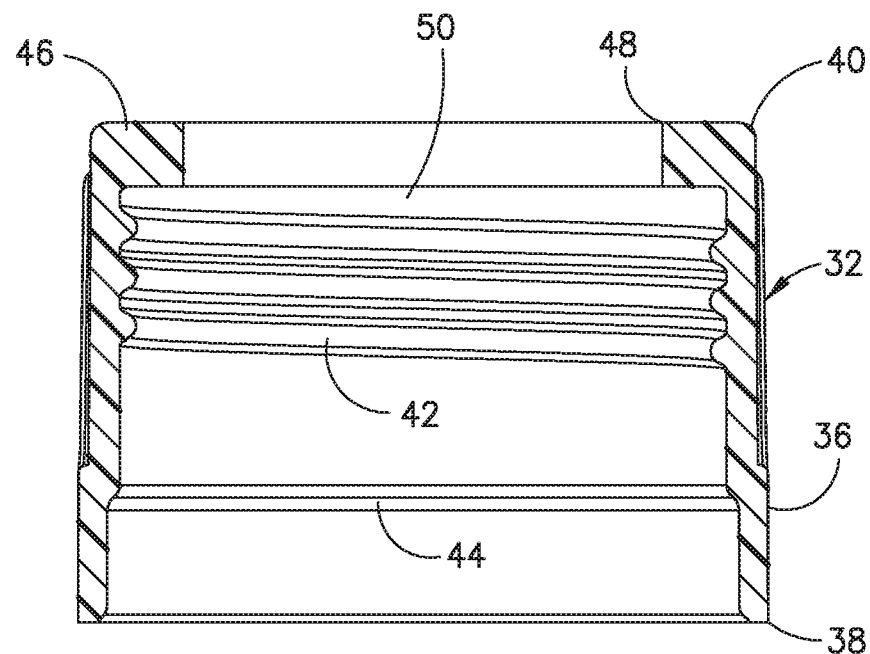
FIG. 8 is a cross-sectional view of the collar of FIG. 6.

The distal end 40 of the sidewall 36 includes an end wall 46. In the embodiment shown, the end wall 46 extends substantially perpendicular to the longitudinal axis of the collar 32. The end wall 46 has an inner edge 48 defining an opening 50 in the distal end 40 of the collar 32 as shown in FIGS. 6-8.

Figure 9:
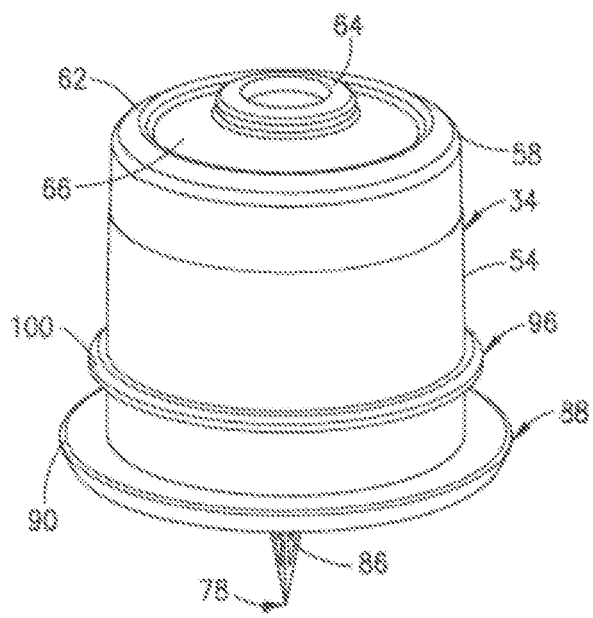
FIG. 9 is a perspective view of the needle hub in the embodiment of FIG. 3.
Figure 10:
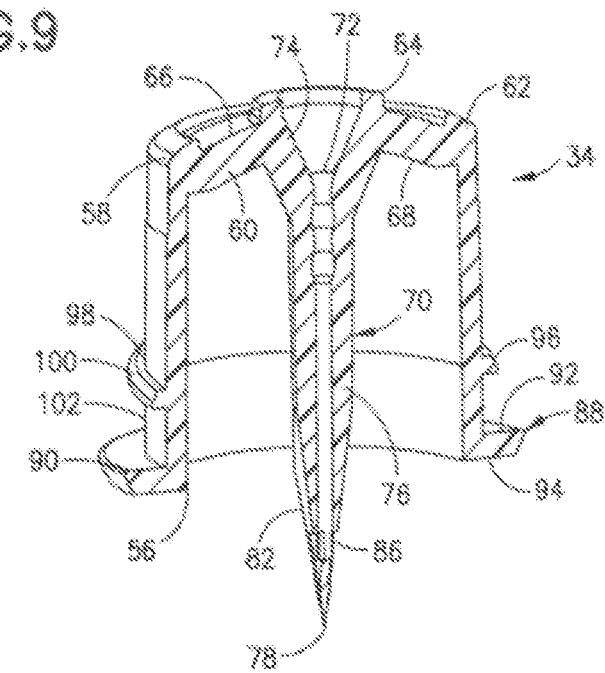
FIG. 10 is a perspective view in cross-section of the needle hub.
Figure 11:
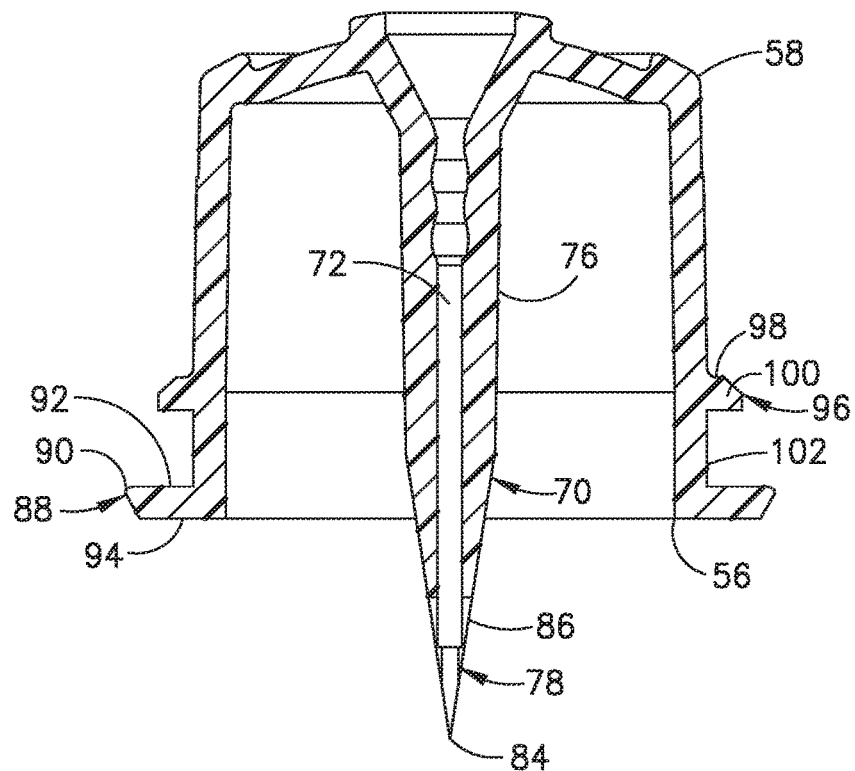
FIG. 11 is a side view in cross-section of the needle hub.

The needle hub 34 has a shape and configuration for supporting a needle 52 as shown in FIG. 4. Referring to FIG. 9-11, the needle has a lumen for delivering the drug or other substance to the patient as known in the art. The needle 52 has a length and gauge commonly used in pen needles. In one embodiment, the needle can have length of about 3-4 mm although length can be selected according to the intended use and intended depth of penetration into the skin of the patient. Needle hub 34 is connected to the collar 32 and is freely rotatable relative to the collar about a longitudinal axis of the pen needle 30.

In the embodiment shown, the needle hub 34 is formed by a sidewall 54 having an open proximal end 56 and a closed distal end 58. In the embodiment shown, the sidewall 54 has a substantially cylindrical configuration although other shapes and dimensions can be used. The distal end 58 of the needle hub 34 has an end wall 60 closing the distal end of the needle hub and defining a skin contact surface for contacting the patient and limiting the depth of penetration of the needle during the delivery of the substance into the patient. In the embodiment shown, the end wall 60 has an outer annular ring 62 and an inner post 64 forming a skin contact surface. A recessed area 66 is formed between the outer ring 62 and the inner post 64 forming part of the skin contact surface of the needle hub. The contour and position of the inner and outer rings relative to each other control the deformation of the skin when the needle is inserted into the patient and the skin contact surface is pressed against the skin by a common insertion force by the user. As shown in FIG. 10, the outer ring 62, inner ring 64 and recessed portion 66 form a conical, convex shape.

The end wall 60 has an inner surface 68 with a projection 70 extending toward the proximal end of the needle hub. In the embodiment shown, the projection 70 forms a spike or lance and has a length greater than the longitudinal dimension of the side wall 54 of the needle hub 34 so that the projection 70 extends into the collar as shown FIG. 4. An axial passage 72 defining a lumen extends through the projection 70 and the end wall 60. The axial passage 72 receives and supports the needle 52 as shown in FIG. 4 and provides fluid communication between the lumen of the needle 52 and the lumen of the projection 70. A conical shaped portion 74 of the projection 70 is formed in the end wall 64 for receiving an adhesive to bond the needle 52 to the needle hub. For purposes of clarity, the adhesive is not illustrated.

Figure 12:
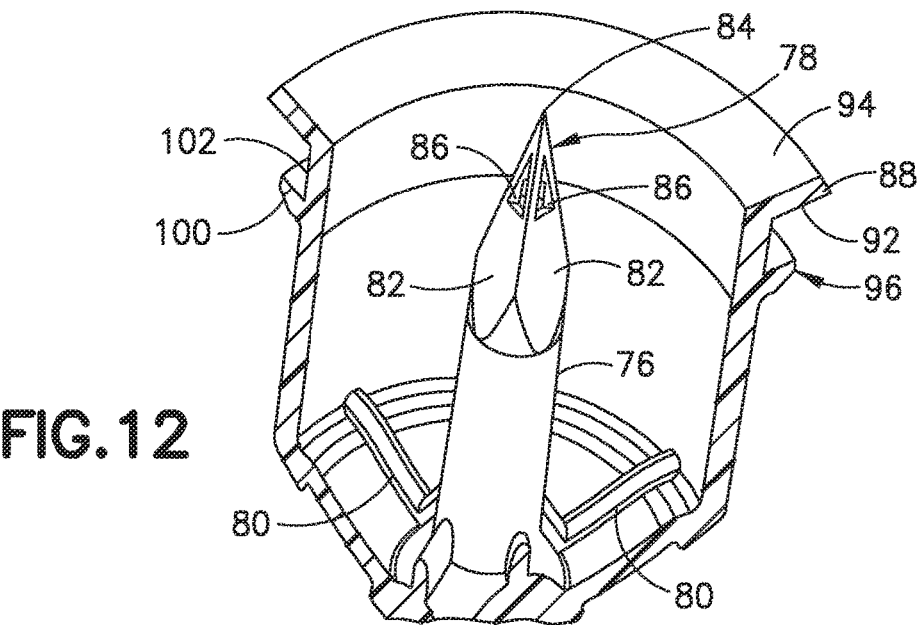
FIG. 12 is a bottom perspective view of the needle hub showing the projection.

Referring to FIG. 10, the projection 70 has a substantially cylindrical body 76 terminating at a sharp or pointed tip 78. The sharp tip 78 forms a closed distal end and is configured for piercing the septum 106 of the delivery device when the pen needle 30 is attached to the delivery device. The axial passage 72 extends between the tip 78 and the end wall 60 providing a fluid communication through the projection 70 to the needle 52. Radially extending ribs 80 are formed on the inner surface of the end wall 60 as shown in FIG. 12 to assist in stabilizing the projection 70 and strengthening the end wall 60. The needle 52 is positioned in the distal end of the axial passage 72. In embodiments of the device, the projection 70 is a separate element from the needle 52 and the proximal end of the needle is inserted into the axial passage 72 to communicate with the lumen of the projection 70. The needle is typically made of stainless steel and the needle hub is typically made of a plastic material. The projection in the embodiments shown is integrally formed with the needle hub as in a one-piece molded unit. In other embodiments, the projection can be a separate member that is attached to the needle hub by a suitable attachment mechanism. The needle can be attached by a suitable adhesive to the distal end of the needle hub.

Figure 13:
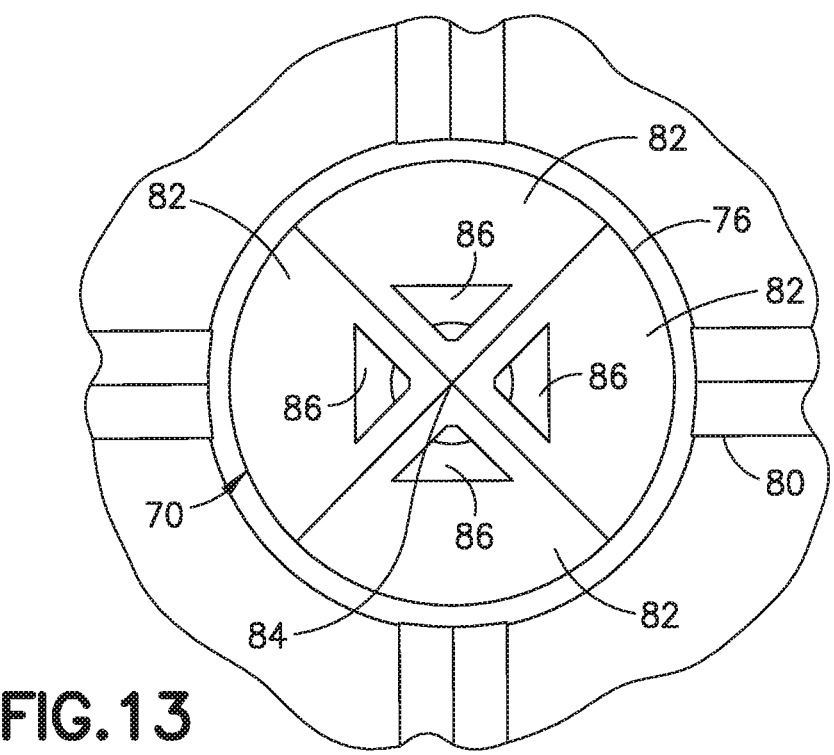
FIG. 13 is a bottom end view of the projection of FIG. 12.

The tip 78 of the projection 70 can have various shapes and configurations for providing a sharp or pointed tip that will effectively pierce the septum while ensuring fluid communication from the delivery device to the needle 52. Referring to FIGS. 12 and 13, the tip 78 can be formed by beveled faces 82 that converge to a point 84. The beveled faces 82 can be flat as shown, can have a convex contour, or a concave contour. In the embodiment shown, each of the beveled faces 82 is formed with an opening 86 communicating with the axial passage 72 providing the fluid communication to the needle. The opening 86 are preferably spaced axially form the point 84 so that the openings do not interfere with the projection piercing the septum of the delivery device and the openings do not cause coring of the septum. The opening 86 have a shape and dimension to provide sufficient flow of the medication from the delivery device to the needle. In the embodiment shown, the openings 86 have a generally triangular shape although other shapes can be used. In the embodiment shown, four beveled surfaces are provided although the number of beveled surfaces can vary depending on the diameter and length of the projection.

Figure 14:
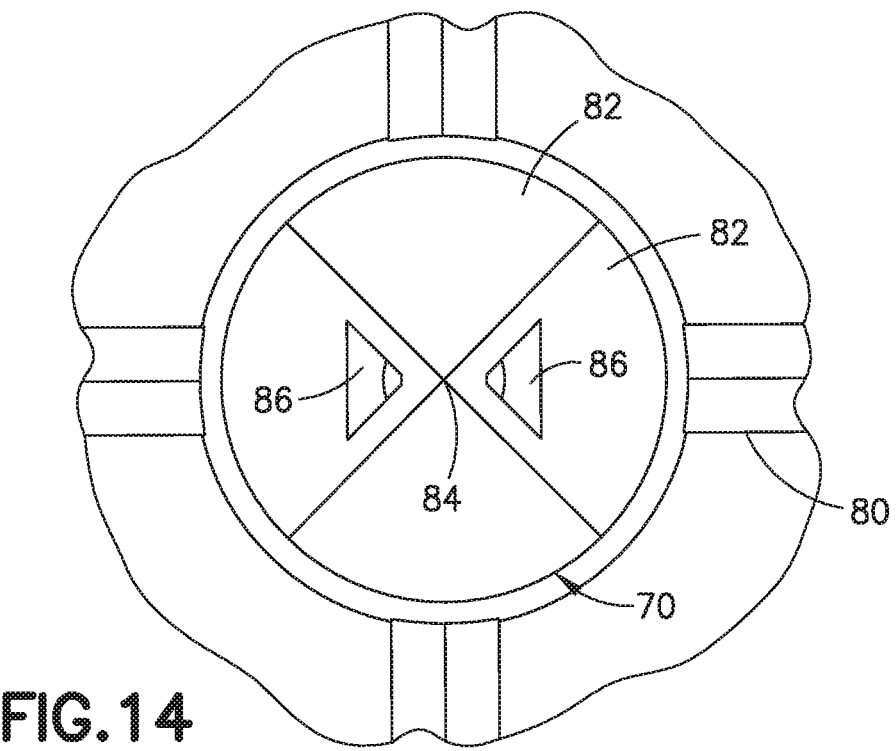
FIG. 14 is a bottom end view of the projection in an alternative embodiment.
Figure 15:
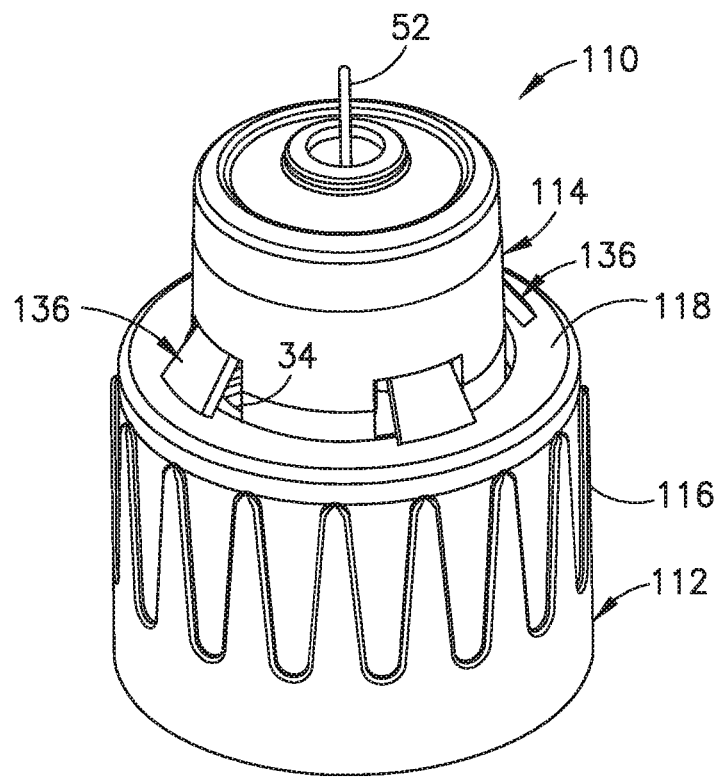
FIG. 15 is a perspective view of the pen needle in a second embodiment.

In an alternative embodiment shown in FIG. 14, the tip 78 of the projection 70 can be formed by the beveled faces 82 where fewer than all of the beveled faces include an opening 86. In the embodiment shown in FIG. 14, two openings 86 are provided on opposite beveled faces 82. The openings are located relative to the beveled surfaces and the tip of the projection to provide effective delivery of the substance from the reservoir of the delivery pen and the needle for delivering a desired dosage and flow rate to the patient.

The proximal end 56 of the needle hub 34 is formed with a coupling for connecting the needle hub 34 to the collar 32 while allowing rotation between the needle hub and the collar. In the embodiment shown in FIGS. 9-12, the coupling is formed by an annular flange 88 extending radially outward from the proximal end of the sidewall 54 of the needle hub 34. The flange 88 has a peripheral edge 90 complementing the inner dimension of the collar 32 as shown in FIG. 5, the sidewall 54 of the needle hub 34 has a dimension complementing the opening 50 in the collar whereby the needle hub 34 can rotate within the opening in the collar. The flange 88 has a top face 92 shown in FIG. 10 with a surface complementing the bottom surface of the end wall 46 of the collar 32. In the embodiment shown, the top face 92 is a substantially flat surface extending radially outward from the longitudinal axis of the needle hub 34. The bottom face 94 of the flange 88 shown in FIG. 10 also has a substantially flat radially extending surface for mating with the end of the delivery device 10 of the collar 32.

The coupling mechanism in the embodiment shown also includes a second flange 96 extending radially outward from the sidewall 54 of the needle hub 34. The second flange 96 is spaced from the flange 88 a distance corresponding substantially to the thickness of the end wall 46. As shown in FIGS. 9 and 10, the flange 96 has a radial dimension less than the radial dimension of the flange 88. The flange 96 has a top face 98 with a chamfered edge 100. The chamfered edge 100 is able to slide over the inner edge of the opening 50 in the end wall 46 by a snap connection to couple the needle hub 34 to the collar 32. As shown in FIG. 4, the needle hub 34 is coupled to the collar 32 by the end wall 46 captured in the recess 102 between the flange 88 of the flange 96. The collar 32 and the hub 34 are connected together so that the needle hub can rotate freely in the open end of the collar 32.

The pen needle 30 is connected to the threaded end of the delivery device 10 as shown in FIG. 5. The collar 32 is rotated as indicated by arrow 104 shown in FIG. 5 to advance the pen needle onto the delivery device 10. The collar 32 rotates to screw the collar onto the threaded end of the delivery device. The needle hub 34 is able to remain rotationally fixed relative to the collar 34 so that the needle hub 34 moves toward the septum 106 in a linear direction indicated by arrow 108 in FIG. 5 substantially without rotational movement of the needle hub 34. The projection 70 is able to pierce the septum 60 by moving in a substantially linear direction without twisting or rotation of the projection relative to the septum of the delivery device. As shown in FIG. 5, screwing the collar onto the delivery device enables the projection 70 to pierce the septum to access the contents of the delivery device and provide the fluid communication between the delivery device and the needle 52. In one embodiment, the end of the projection 70 is spaced inwardly from the proximal end of the collar 32 so that the threads of the collar engage the threads of the delivery device before the projection engages the septum. Rotating the collar 32 relative to the delivery device 10 moves the needle hub and projection into engagement with the septum.

The coupling device between the collar and the needle hub can be any suitable configuration whereby the needle hub is connected to the collar and where the collar and needle hub are able to rotate relative to one another.

In another embodiment shown in FIGS. 15-22, a pen needle 110 includes a collar 112 and a needle hub 114. Collar 112 is substantially the same as in the embodiment of FIGS. 3-14 where the collar 112 includes a sidewall 116, and an end wall 118 forming an inwardly extending flange with an inner edge forming an opening 120.

Figure 20:
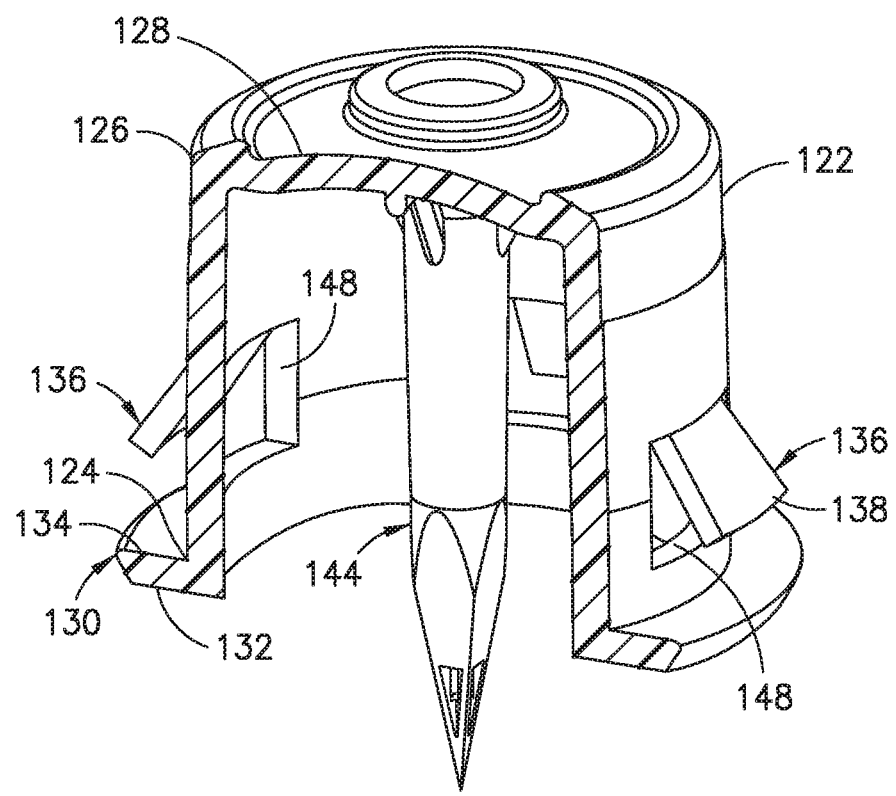
FIG. 20 is a top perspective view in cross-section showing the projection.
Figure 21:
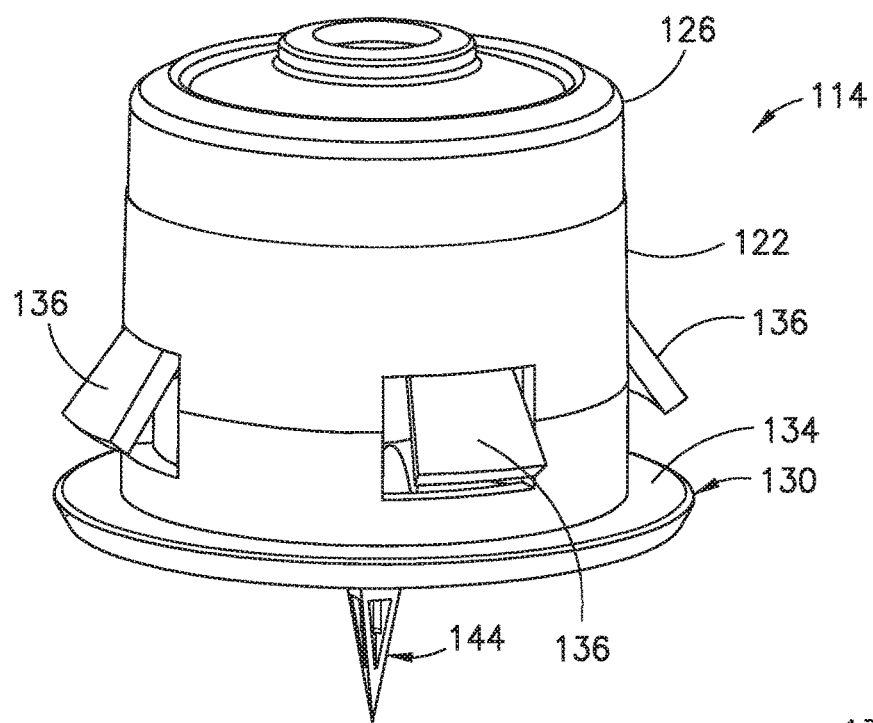
FIG. 21 is a perspective view of the needle hub of the embodiment of FIG. 15.
Figure 22:
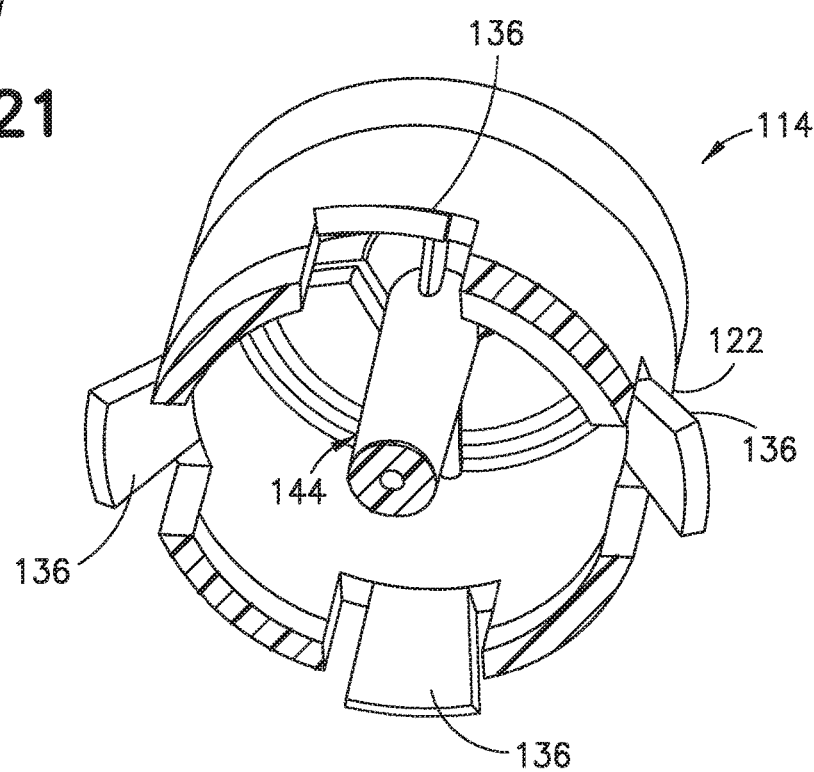
FIG. 22 is a bottom perspective view of the needle hub.

Needle hub 114 is similar to the needle hub in the previous embodiment. Referring to FIGS. 20-22, needle hub 114 has a sidewall 122 with a substantially cylindrical configuration with a proximal end 124 and a distal end 126. An end wall 128 is formed at the distal end 126 for supporting the needle 52 as in the previous embodiment. The end wall 128 in the embodiment shown has an inner post and outer ring forming the skin contact surface in a manner similar to the previous embodiment.

Figure 18:
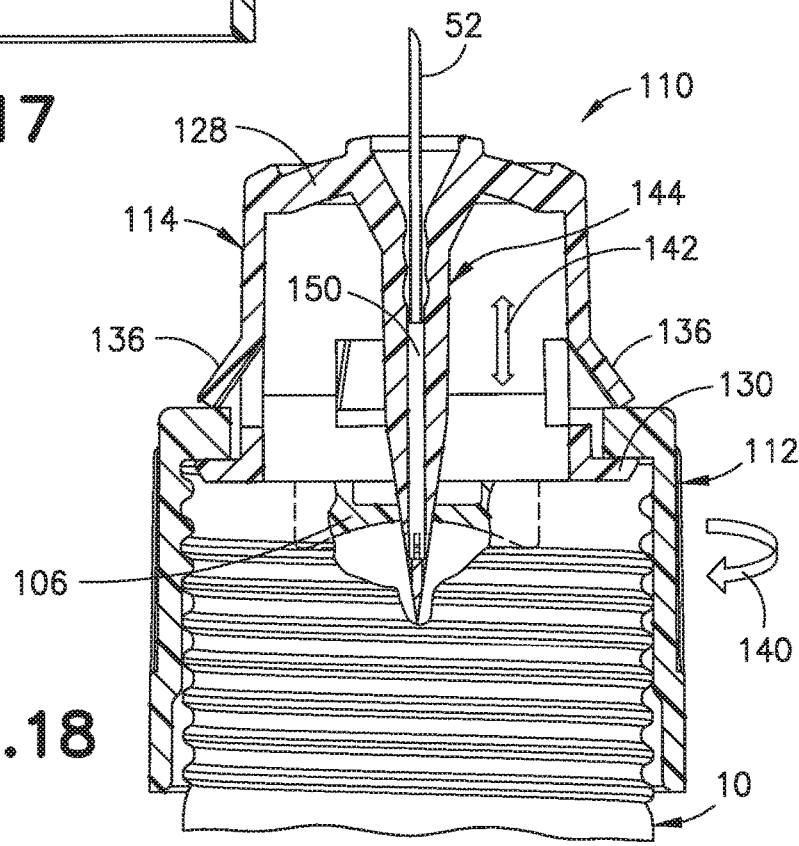
FIG. 18 is a cross-sectional view showing the pen needle coupled to the delivery device.
Figure 19:
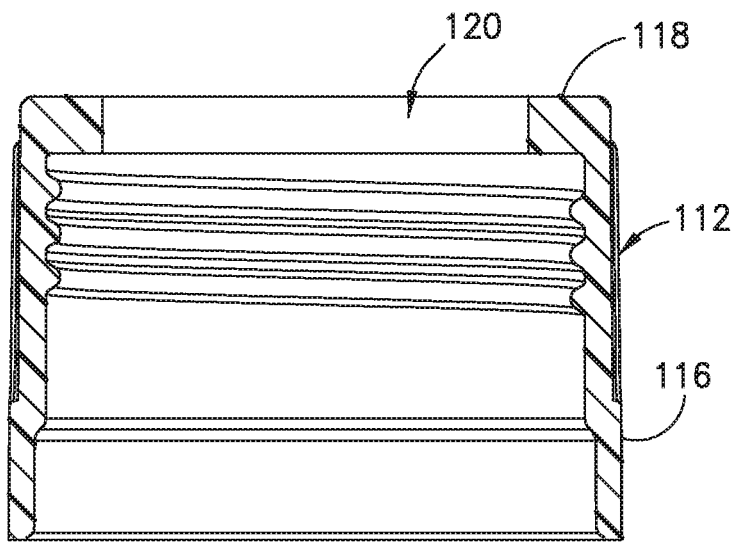
FIG. 19 is a cross sectional view of the collar.

The proximal end 124 of the sidewall 122 includes an outwardly extending flange 130 with a dimension complementing the inner dimension of the collar 112. The flange 130 has a bottom face 132 for mating with the end of the delivery device as shown in FIG. 18 and a top face 134 for contacting the bottom face of the inwardly extending flange 118 of the collar 112. The needle hub 114 includes a projection 144 extending axially from the end wall 128 for piercing the septum having a lumen 150 supporting the needle 52 as in the previous embodiment. The projection 144 is substantially the same as in the previous embodiment.

Figure 16:
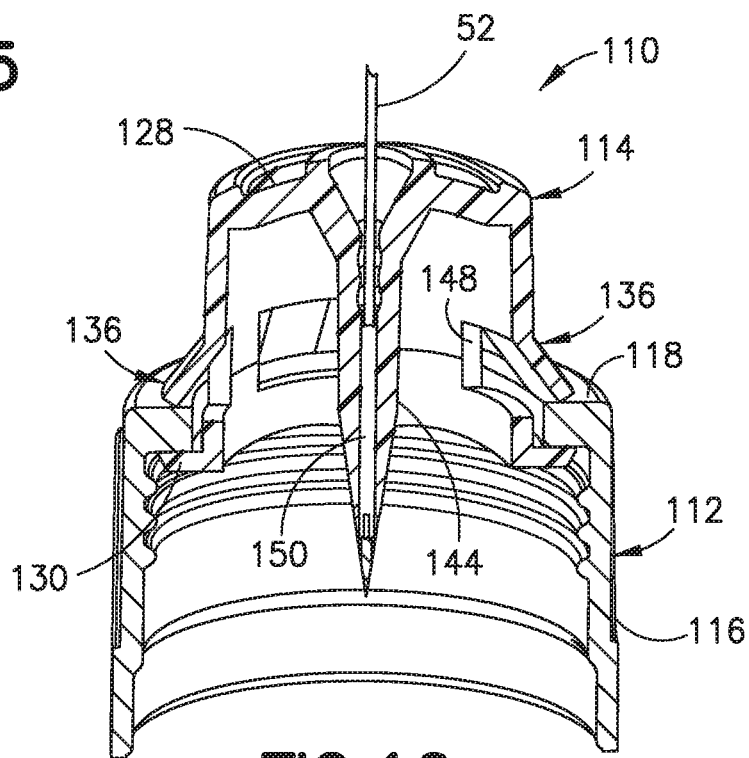
FIG. 16 is a perspective view in cross-section of the pen needle of FIG. 15.
Figure 17:
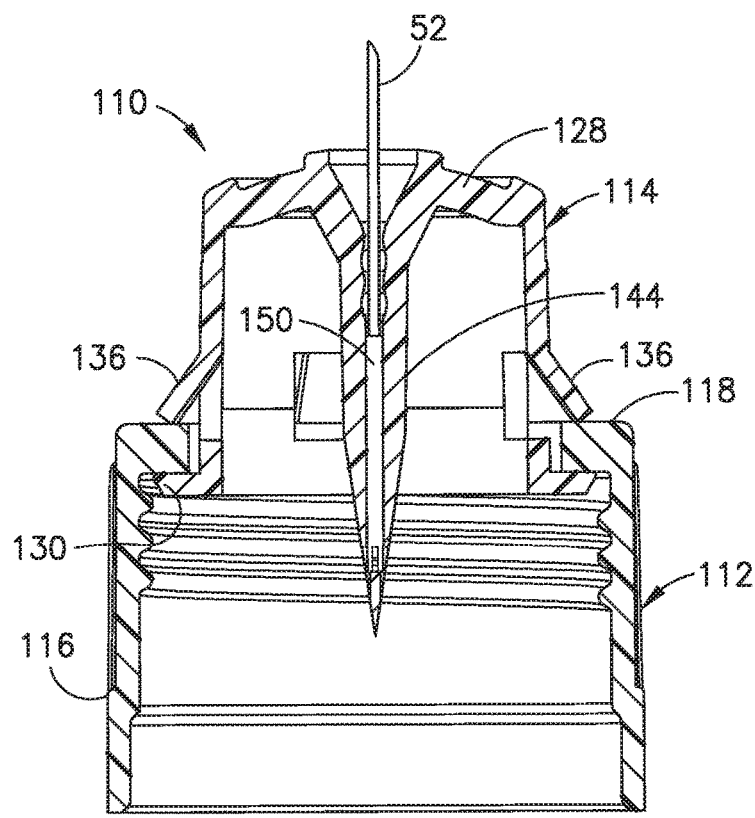
FIG. 17 is a cross-sectional side view of the pen needle of FIG. 15.

The coupling between the collar 112 and needle hub 114 in the embodiment shown includes at least one and typically a plurality of tabs 136. The tabs 136 are formed by cutouts 148 in the sidewall 122. As shown in FIG. 16, the tabs 136 are integrally formed with the sidewall 122 and project outwardly at an incline from the sidewall towards the proximal end of the needle hub and form an annular recess between the end of the tabs 136 and the flange 130. The tabs 136 have a first end connected to the sidewall and a free end 138 for contacting the flange 118 of the collar 112. The tabs 136 are sufficiently flexible so that the needle hub can be connected to the collar 112 by sliding the needle hub through the opening in the collar whereby the tabs 136 are able to slide past the end wall or flange 118 of the collar 112 and snap outwardly to the position shown in FIG. 16. In the embodiment shown, the needle hub includes four tabs 136 although the number of tabs can be more or less than four as needed to retain the needle hub on the collar without inhibiting rotation of the needle hub relative to the collar.

Referring to FIG. 18, the pen needle 110 is connected to the delivery device by screwing the collar 112 onto the threaded end of the delivery device in the direction of arrow 140. Rotation of the collar 112 is independent of the needle hub 114 so that the needle hub moves in a linear direction without rotation. The needle hub 114 is able to move axially without rotation so that the projection is able to pierce the septum in a linear direction indicated by arrow 142 to form the fluid communication between the delivery device and the needle.

The foregoing embodiments and advantages are exemplary and are not to be construed as limiting the scope of the present invention. The description of an exemplary embodiment of the present invention is intended to be illustrative, and not to limit the scope of the present invention. Various modifications, alternatives, and variations will be apparent to those of ordinary skill in the art, and are intended to fall within the scope of the invention. It is particularly noted that the features of different embodiments and claims may be combined with each other as long as they do not contradict each other. Accordingly, all such modifications are intended to be included within the scope of this invention as defined in the appended claims and their equivalents.

The invention claimed is:

1. A pen needle comprising:
a collar having a side wall, an open proximal end, and a distal end; and
a needle hub rotatably coupled to said distal end of said collar, said needle hub having a proximal end and a distal end, a needle extending from said distal end, and a projection at said proximal end of said needle hub configured for piercing a septum of a delivery device, where said collar is rotatable independently of said needle hub, wherein said projection is a spike integrally formed with said needle hub and extends axially from said proximal end of said needle hub.

2. The pen needle of claim 1, wherein said side wall of said collar has internal threads configured for coupling to the delivery device.

3. The pen needle of claim 2, wherein said collar has an opening in said distal end, and where said needle hub is rotatable within said opening in said collar.

4. The pen needle of claim 3, wherein said distal end of said collar has an end wall; and where said proximal end of said needle hub has an annular recess receiving said end wall of said collar.

5. The pen needle of claim 4, wherein said needle hub has a first flange at said proximal end, and a second flange spaced from said first flange to define said annular recess of said needle hub between said first flange and second flange.

6. The pen needle of claim 1, wherein said proximal end of said needle hub is configured for mating with a distal end of said delivery device.

7. The pen needle of claim 1, wherein said projection has a distal end with at least one beveled surface, and where said projection has an inlet opening communicating with a lumen in said projection, and where said needle is in fluid communication with said lumen.

8. The pen needle of claim 7, wherein said inlet opening of said projection is formed in said at least one beveled surface.

9. The pen needle of claim 1, wherein said needle hub has a side wall with a proximal end and a distal end, and an end wall at said distal end.

10. The pen needle of claim 1, wherein said needle hub has a side wall with an outwardly extending flange at said proximal end of said needle hub, and at least one outwardly extending tab spaced from said flange, and where said distal end of said collar is captured between said flange and said at least one tab to couple said needle hub to said collar, where said collar is rotatable relative to said needle hub.

11. The pen needle of claim 10, wherein said side wall of said needle hub includes a plurality of said tabs spaced around said side wall.

12. A pen needle comprising:
a collar having a side wall, an open proximal end having a coupling configured for coupling to a delivery device, and a distal end with a central opening;
a needle hub having a proximal end and a distal end, said proximal end of said needle hub having a coupling member coupled to said distal end of said collar where said needle hub is rotatable independently of said collar about a longitudinal axis of said pen needle;
a needle extending from said distal end of said needle hub; and
a projection having a lumen receiving said needle and extending from said proximal end of said needle hub, said projection configured for piercing a septum of the delivery device and having an opening providing fluid communication between the delivery device and said needle wherein said projection is a spike integrally formed with said needle hub and extends axially from said proximal end of said needle hub.

13. The pen needle of claim 12, wherein the needle hub has a side wall and an end wall at said distal end of said needle hub.

14. The pen needle of claim 13, wherein said side wall of said needle hub has an outwardly extending first flange at said proximal end, and a coupling member extending outwardly from said side wall of said needle hub and spaced from said first flange forming a recess receiving a flange on said collar extending inwardly toward said central opening.

15. The pen needle of claim 14, wherein said coupling member is a second flange.

16. The pen needle of claim 14, wherein said coupling member is at least one tab projecting outwardly from said side wall and spaced from said first flange.

17. The pen needle of claim 16, wherein said at least one tab is flexible.

18. The pen needle of claim 14, wherein said coupling member comprises a plurality of flexible tabs spaced from said first flange to define an annular recess, said distal end of said collar having a flange extending radially inward to define said central opening, and where said flange on said collar is received in said annular recess of said needle hub.

19. The pen needle of claim 18, wherein said plurality of flexible tabs project outwardly from said side wall of said needle hub toward said first flange at an incline relative to the longitudinal axis of said pen needle.

20. The pen needle of claim 19, wherein said plurality of flexible tabs are spaced apart around a periphery of said needle hub.

21. The pen needle of claim 14, wherein said projection has a distal end with a pointed tip for piercing the septum of the delivery device.

22. The pen needle of claim 21, wherein said tip has a plurality of beveled surfaces converging to a sharpened closed end, and where said opening in said projection is formed in at least one of said plurality of beveled surfaces, and is spaced axially from said sharpened closed end.

23. A pen needle comprising:
a collar having a side wall, an open proximal end, and a distal end; and
a needle hub rotatably coupled to said distal end of said collar, said needle hub having a proximal end and a distal end, a needle extending from said distal end, and a projection at said proximal end of said needle hub configured for piercing a septum of a delivery device, where said collar is rotatable independently of said needle hub, wherein said needle hub has a side wall with an outwardly extending flange at said proximal end of said needle hub, and at least one outwardly extending tab spaced from said flange, and where said distal end of said collar is captured between said flange and said at least one tab to couple said needle hub to said collar, where said collar is rotatable relative to said needle hub.

24. A pen needle comprising:
a collar having a side wall, an open proximal end having a coupling configured for coupling to a delivery device, and a distal end with a central opening;
a needle hub having a proximal end and a distal end, said proximal end of said needle hub having a coupling member coupled to said distal end of said collar where said needle hub is rotatable independently of said collar about a longitudinal axis of said pen needle;
a needle extending from said distal end of said needle hub; and
a projection having a lumen receiving said needle and extending from said proximal end of said needle hub, said projection configured for piercing a septum of the delivery device and having an opening providing fluid communication between the delivery device and said needle,
wherein said needle hub has a side wall with an outwardly extending flange at said proximal end of said needle hub, and at least one outwardly extending tab spaced from said flange, and where said distal end of said collar is captured between said flange and said at least one tab to couple said needle hub to said collar, where said collar is rotatable relative to said needle hub.

* * * * *